United States Patent
Decker

(10) Patent No.: US 9,023,319 B2
(45) Date of Patent: May 5, 2015

(54) VACCINE

(75) Inventor: Michael Decker, Bangor, PA (US)

(73) Assignee: Sanofi Pasteur Inc., Swiftwater, PA (US)

( * ) Notice: Subject to any disclaimer, the term of this patent is extended or adjusted under 35 U.S.C. 154(b) by 741 days.

(21) Appl. No.: 11/871,248

(22) Filed: Oct. 12, 2007

(65) Prior Publication Data

US 2008/0206278 A1    Aug. 28, 2008

Related U.S. Application Data

(60) Provisional application No. 60/851,708, filed on Oct. 13, 2006.

(51) Int. Cl.
| | | |
|---|---|---|
| *A61K 49/00* | (2006.01) |
| *A61K 39/145* | (2006.01) |
| *A61K 39/13* | (2006.01) |
| *A61K 39/29* | (2006.01) |
| *A61K 39/102* | (2006.01) |
| *A61K 39/10* | (2006.01) |
| *A61K 39/00* | (2006.01) |

(52) U.S. Cl.
CPC ........... *A61K 39/145* (2013.01); *A61K 2039/54* (2013.01); *A61K 2039/55* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

2004/0053871 A1*  3/2004  Bot et al. ........................ 514/44

OTHER PUBLICATIONS

Ryuzo et al., Antibody Responses to Influenza HA Vaccine in Infants Born before 33 Weeks' Gestation, 2003, Journal of the Japan Pediatric Society, vol. 107, No. 6, pp. abstract.*
Garcia-Canas et al., Approach to the profiling and characterization of influenza vaccine constituents by the combined use of size-exclusion chromatography, gel electrophoresis and mass spectrometry, 2010, Biologicals, vol. 38, pp. 294-302.*
American Lung Association Asthma Clinical Research Centers, "The Safety of Inactivated Influenza Vaccine in Adults and Children with Asthma," N Engl J Med, 345(21): 1529-1536 (2001).
Anderson, Porter "Intrinsic Tritium Labeling of the Capsular Polysaccharide Antigen of *Haemophilus influenzae* Type B," The Journal of Immunology, 120(3): 866-870 (1978).
Barry et al., "Comparative Trial of Influenza Vaccines," American Journal of Epidemiology, 104(1): 47-59 (1976).
Clements et al., "Influenza A Vaccine Decreases the Incidence of Otitis Media in 6- to 30-Month-Old Children in Day Care," Arch Pediatr Adolesc Med, 149: 1113-1117 (1995).

DeStefano et al., "Simultaneous Administration of Influenza and Pneumococcal Vaccines," JAMA, 247: 2551-2554 (1982).
Fischer et al., "Influence of trivalent influenza vaccine on serum theophylline levels," CMA, 126: 1312-1313 (1982).
Grilli et al., "Simultaneous influenza and pneumococcal vaccination in elderly individuals," European Journal of Epidemiology, 13: 287-291 (1997).
Groothuis et al., "Immunization of High-Risk Infants Younger Than 18 Months of Age with Split-Product Influenza Vaccine," Pediatrics, 87(6): 823-828 (1991).
Hoberman et al., "Effectiveness of Inactivated Influenza Vaccine in Preventing Acute Otitis Media in Young Children," JAMA, 290(12): 1608-1616 (2003).
Honkanen et al., "Reactions Following Administration of Influenza Vaccine Alone or With Pneumococcal Vaccine to the Elderly," Arch Intern Med, 156: 205-208 (1996).
Hurwitz et al., "Studies of the 1996-1997 Inactivated Influenza Vaccine among Children Attending Day Care: Immunologic Response, Protection against Infection, and Clinical Effectiveness," The Journal of Infectious Diseases, 182: 1218-1221 (2000).
Kanra et al., "Comparison of immunogenicity and tolerability of a virosome-adjuvanted and a split influenza vaccine in children," Pediatr Infect Dis J, 23(4): 300-306 (2004).
Kawasaki et al., "Bilateral Anterior Ischemic Optic Neuropathy Following Influenza Vaccination," Journal of Neuro-Ophthalmology, 18(1): 56-59 (1998).
Kelsall et al., "Microscopic Polyangiitis After Influenza Vaccination," J. Rheumatol, 24: 1198-1202 (1997).
Kramer et al., "Effect of influenza vaccine on warfarin anticoagulation," Clin. Pharmacol. Ther., 35(3): 416-418 (1984).
Leder et al., "Travel Vaccines and Elderly Persons: Review of Vaccines Available in the United States," Clinical Infectious Diseases, 33: 1553-1566 (2001).
Levine et al., "Increased serum phenytoin concentration following influenza vaccination," Clinical Pharmacy, 3: 505-509 (1984).
Lipsky et al., "Influenza Vaccination and Warfarin Anticoagulation," Annals of Internal Medicine, 100: 835-837 (1984).
Morbidity and Mortality Weekly Report—Recommendations of the Advisory Committee on Immunization Practices (ACIP), "Prevention and Control of Influenza," Recommendations and Reports, 51(RR-3): 1-36 (2002).
Murphy et al., "Safe administration of influenza vaccine in asthmatic children hypersensitive to egg proteins," The Journal of Pediatrics, 106(6): 931-933 (1985).
Neuzil et al., "Efficacy of inactivated and cold-adapted vaccines against influenza A infection, 1985 to 1990: the pediatric experience," Pediatr Infect Dis J, 20(8): 733-740 (2001).
Renton et al., " Decreased elimination of theophylline after influenza vaccination," CMA Journal, 123: 288-290 (1980).
Retailliau et al., "Illness After Influenza Vaccination Reported Through a Nationwide Surveillance System, 1976-1977," Epidemiol, 111(3): 270-278 (1980).

(Continued)

*Primary Examiner* — Benjamin P Blumel
(74) *Attorney, Agent, or Firm* — Choate, Hall & Stewart LLP; Fangli Chen

(57) ABSTRACT

Provided herein are methods for immunizing children under six months of age by administering to the child a pharmaceutical composition comprising at least one antigen derived from an influenza virus.

8 Claims, 3 Drawing Sheets

(56) References Cited

OTHER PUBLICATIONS

Rothbarth et al., "Sense and Nonsense of Influenza Vaccination in Asthma and Chronic Obstructive Pulmonary Disease," Am J Respir Crit Care Med, 151: 1682-1686 (1995).

Schonberger et al., "Guillain-Barre Syndrome Following Vaccination in the National Influenza Immunization Program, United States, 1976-1977," American Journal of Epidemiology, 110(2): 105-123 (1979).

Terebuh et al., "Impact of influenza on young children and the shaping of United States influenza vaccine policy," Pediatr Infect Dis J, 22(10): S231-S235 (2003).

Thompson et al., "Mortality Associated With Influenza and Respiratory Syncytial Virus in the United States," JAMA, 289: 179-186 (2003).

* cited by examiner

*Influenza A/H1N1*

Reverse Cumulative Distribution Curves
Flu A/New Caldonia/20/99 (H1N1)
Intent-to-Treat Population ——— Fluzone (N = 747

- - - - - - - - Placebo (N = 349)

*Influenza A/H3N2*

Reverse Cumulative Distribution Curves
Flu A/New York/55/2004 (H3N2)
Intent-to-Treat Population

*Influenza B*

Reverse Cumulative Distribution Curves
Flu B/jiangsu/10/2003
Intent-to-Treat Population _____ Fluzone (N = 747

- - - - - - - - Placebo (N = 349)

VACCINE

This application claims the benefit of U.S. provisional application No. 60/851,708 filed on Oct. 13, 2006. The above-mentioned provisional application is hereby incorporated by reference in its entirety.

FIELD OF THE INVENTION

This invention relates to the field of influenza vaccines.

BACKGROUND

Influenza A viruses are classified into subtypes on the basis of two surface antigens: hemagglutinin (H) and neuraminidase (N). Three subtypes of hemagglutinin (H1, H2, and H3) and two subtypes of neuraminidase (N1 and N2) are recognized among influenza A viruses that have caused widespread human disease. Immunity to these antigens—especially to the hemagglutinin—reduces the likelihood of infection and lessens the severity of disease if infection occurs. Infection with a virus of one subtype confers little or no protection against viruses of other subtypes. Furthermore, over time, antigenic variation (antigenic drift) within a subtype may be so marked that infection or vaccination with one strain may not induce immunity to distantly related strains of the same subtype. Although influenza B viruses have shown more antigenic stability than influenza A viruses, antigenic variation does occur. For these reasons, major epidemics of respiratory disease caused by new variants of influenza continue to occur.

Young children are at high risk for influenza-related disease and complications. Children <6 months of age have the highest rates of hospitalization and medically-attended illnesses of any age group, but there is no licensed influenza vaccine for this age range. It is known in the art that immunogenicity of flu vaccines is inconsistent and generally poor in infants younger than 6 months (Groothuis et al. Immunization of high-risk infants younger than 18 months of age with split-product influenza vaccine. *Pediatrics.* 1991; 87: 823-828; Groothuis et al. Immune response to split-product influenza vaccine in preterm and full-term young children. *Vaccine.* 1992; 10: 221-225). The present invention provides compositions and methods for using such compositions to successfully immunize children younger than six months against influenza.

SUMMARY

Figure 1:
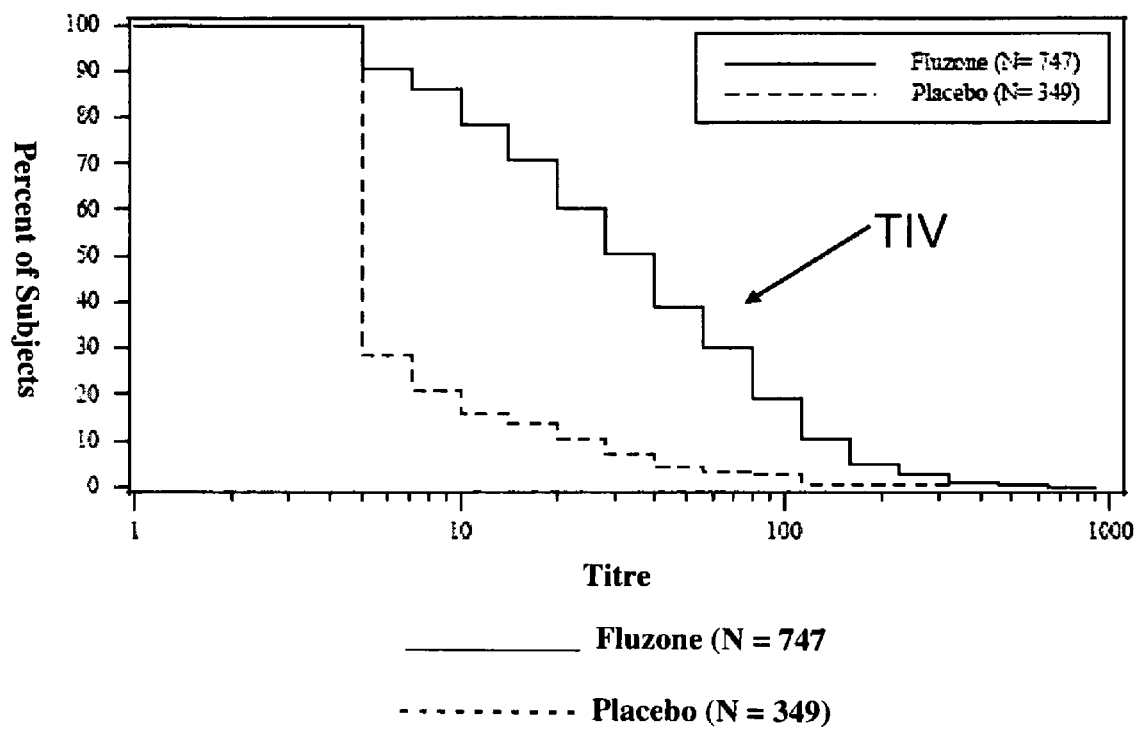
FIG. 1. Reverse cumulative distribution curve showing the immune response against Influenza A/H1N1.

Provided herein are methods for immunizing children under six months of age by administering to the child a pharmaceutical composition comprising at least one antigen derived from an influenza virus.

DETAILED DESCRIPTION

Provided herein are reagents and methodologies useful for treating and/or preventing disease caused by influenza viruses by stimulating an immune response against an antigen derived therefrom. As used herein, an "antigen" is an agent (such as a live, inactivated or killed virus, or fragment thereof) that produces an immune response in a host following administration of the agent thereto. The immune response may be induced de novo or may currently be present or may have been present in the past and is enhanced or re-activated following exposure to antigen. In certain cases, it is preferred that the immune response observed in vivo protects the host from infection by an exogenous organism such that the immune response is "protective". In others, the immune response may assist the host in overcoming an existing infection by an exogenous organism; such immune responses are termed "therapeutic". The immune response may include, for example, the production of antibodies that bind to at least one epitope of the antigen and/or the generation of a cellular immune response against cells expressing an epitope of the antigen. The immune response may be detected by observing, for example, increased antibody production, production of antibodies with increased affinity for the antigen, or an increased cellular response (i.e., increased T cells) against the antigen. An antigen that produces such an immune response may alternatively be referred to as being immunogenic or as an immunogen. Additional immunomodulating agent(s) (i.e., immunomodulator(s)) may be co-administered with an antigen to directly or indirectly induce or enhance the immune response against the antigen above that which would occur upon administration of the antigen alone. Such an agent is considered immuno-stimulatoty or an immune stimulator. Compositions embodying certain aspects of the invention may be, among others, "pharmaceutical" (i.e., contain an active agent and a pharmaceutically acceptable carrier and may or may not generate an immune response), "immunological" (i.e., capable of inducing an immune response following administration in a host following administration of the composition thereto), or "vaccines" (i.e., capable of producing a protective or therapeutic immune response in a host following administration of the composition thereto). An antigen or multiple antigens may or may not be combined with an agent having immunomodulatory activity.

Many compositions may be suitable for use in delivering the influenza antigen to the host. These may include whole virus vaccines consisting of inactivated viruses; split virus vaccines consisting of virus particles disrupted by detergent treatment; or sub-unit vaccines consisting essentially of haemagglutinin and neuraminidase from which other virus components have been removed; protein subunit vaccines (i.e., encoded by "naked DNA" or adenovirus vectors), adjuvanted (i.e., MF59); live, attenuated influenza virus vaccines (i.e., intransal vaccine) may also be suitable. In one embodiment, the commercial vaccine (Fluzone®) is utilized. This vaccine is a sterile suspension prepared from influenza virus propagated in chicken embryos. The virus-containing allantoic fluids are harvested and inactivated with formaldehyde. The virus is then concentrated and purified in a linear sucrose density gradient solution, using a continuous flow centrifuge. The virus is then chemically disrupted using Triton® X-producing a split-antigen. The split-antigen is then further purified by chemical means and suspended in sodium phosphate-buffered isotonic sodium chloride solution. Gelatin (0.05%) is then added as a stabilizer and thimerosol (1:10,000) is added as a preservative. Thimerosol-free preparations may also be suitable. Other preparations containing influenza antigens may also be suitable.

In certain embodiments, the antigen is co-administered with an agent having immunomodulatory activity (i.e., an immunomodulator). Immunomodulators may be separate from the antigen or may form a single unit with the antigen in any suitable manner such as, for example, as a fusion protein. Many suitable immunomodulators are known in the art. It is preferred that the agent be immune stimulator. For example, in certain embodiments, the antigen is administered in combination with one or more adjuvants. Exemplary adjuvants include, for example, those listed in Table I:

TABLE I

Types of Immunologic Adjuvants

| Type of Adjuvant | General Examples | Specific Examples/References |
|---|---|---|
| Gel-type | Aluminum hydroxide/phosphate ("alum adjuvants") | (Aggerbeck and Heron, 1995) |
| | Calcium phosphate | (Relyveld, 1986) |
| Microbial | Muramyl dipeptide (MDP) | (Chedid et al., 1986) |
| | Bacterial exotoxins | Cholera toxin (CT), *E. coli* labile toxin (LT)(Freytag and Clements, 1999) |
| | Endotoxin-based adjuvants | Monophosphoryl lipid A (MPL) (Ulrich and Myers, 1995) |
| | Other bacterial | CpG oligonucleotides (Corral and Petray, 2000), BCG sequences (Krieg, et al. Nature, 374: 576), tetanus toxoid (Rice, et al. J. Immunol., 2001, 167: 1558-1565) |
| Particulate | Biodegradable Polymer microspheres | (Gupta et al., 1998) |
| | Immunostimulatory complexes (ISCOMs) | (Morein and Bengtsson, 1999) |
| | Liposomes | (Wassef et al., 1994) |
| Oil-emulsion and surfactant-based adjuvants | Freund's incomplete adjuvant | (Jensen et al., 1998) |
| | Microfluidized emulsions | MF59 (Ott et al., 1995) SAF (Allison and Byars, 1992) (Allison, 1999) |
| | Saponins | QS-21 (Kensil, 1996) |
| Synthetic | Muramyl peptide derivatives | Murabutide (Lederer, 1986) Threony-MDP (Allison, 1997) |
| | Nonionic block copolymers | L121 (Allison, 1999) |
| | Polyphosphazene (PCPP) | (Payne et al., 1995) |
| | Synthetic polynucleotides | Poly A: U, Poly I: C (Johnson, 1994) |
| | Thalidomide derivatives | CC-4047/ACTIMID (J. Immunol., 168(10): 4914-9) |

In other embodiments, it may be desirable to include one or more cytokines and/or chemokines as the immunomodulator(s) either alone or with an adjuvant. Suitable cytokines include, for example, any of the interleukins such as interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. *Vaccine*, 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), and/or interferons such as IFN-α or INF-γ. Suitable chemokines include but are not limited to CXCL10 (IP-10), CCL7 (MCP-3) (Biragyn, et al. *Nature Biotech.* 1999, 17: 253-258), CCL3 (MIP-1α) and CCL5 (RANTES) (Boyer, et al. *Vaccine,* 1999, 17 (Supp. 2): S53-S64). Many other cytokines suitable for use in practicing the present invention are known in the art.

While the compositions of the invention can be administered as the sole active pharmaceutical agent, they can also be used in combination with one or more other compositions or agents (i.e., other vaccines, immunomodulators, antibiotics).

When administered as a combination, the individual components can be formulated as separate compositions administered at the same time or different times, or the components can be combined as a single composition.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. A prime-boost regimen may also be utilized (WO 01/30382 A1) in which an antigen is initially administered in a priming step in one form followed by a boosting step in which the antigen is re-administered in the same or different form.

A kit comprising a composition of the present invention is also provided. The kit can include a separate container containing a suitable carrier, diluent or excipient, Additionally, the kit can include instructions for mixing or combining ingredients and/or administration.

A better understanding of the present invention and of its many advantages will be had from the following examples, given by way of illustration.

EXAMPLES

Example 1

The data described herein is derived from a prospective, double-blind, randomized study of licensed trivalent inactivated influenza vaccine (Fluzone®) in healthy 2 M old infants ("GRC28"). This trial was conducted at 31 US sites during the fall 2005-winter 2006 season. The subjects were randomized 2:1 to receive via intramuscular (1M) injection a first and second dose of either TIV (Fluzone®; 2005-2005 Influenza A/H1N1/New Caledonia/20/99, Influenza A/H3N2/Flu A/New York/55/2004, and Influenza B/Jiangsu/2003) or placebo at 6-12 weeks of age and 4 weeks later, respectively. Concomitant pediatric vaccines administered under protocol-specified conditions included DTTaP (Daptacel), pneumococcal conjugate (Prevnar), Hib conjugate (ActHIB), inactivated polio (IPOL), and Hepatitis B vaccine. Serum was isolated and assayed for antibodies at four and seven months of age (i.e., after the first and second dose, respectively).

The population of patients participating in this study are shown in Table I. The population in whom serology was determined is shown in Table II,

TABLE I

| | Population | |
|---|---|---|
| Category | TIV | Placebo |
| N | 915 (747) | 460 (349) |
| Males | 52% | 53% |
| Caucasian | 74% | 75% |
| Mean Age (Weeks) | 9.1 | 9.1 |
| Range | (6, 12) | (6, 12) |

TABLE II

| Subjects with Serologic Data | | |
|---|---|---|
| Category | TIV | Placebo |
| N | 747 | 349 |
| Males | 51% | 55% |
| Caucasian | 74% | 76% |
| Mean Age (Weeks) | 9.2 | 9.1 |
| Range | (6, 12) | (6, 12) |

Following administration of the second dose, blood was drawn and the serum analyzed as indicated below:

TABLE III

| Geometric Mean Titer One Month After 2$^{nd}$ Dose Fluzone | | | |
|---|---|---|---|
|  | H1N1 | H3N2 | B |
| Fluzone | 32.9* | 94.8 | 11.4 |
| Placebo | 7.2 | 8.6 | 5.4 |

*All comparisons to placebo are significant at the 0.05 level.

TABLE IV

| Potential Seroprotection (Titers ≥1:40) after Second Dose* (Percer) | | | |
|---|---|---|---|
|  | H1N1 | H3N2 | B |
| Fluzone | 50.1 | 85.6 | 10.9 |
| Placebo | 6.9 | 10.1 | 0.3 |

*All comparisons to placebo are significant at the 0.05 level.

TABLE V

| Infants with Antibody >1:40 Against At Least 1, 2, or All 3 Strains After Second Dose TIV* | | | |
|---|---|---|---|
|  | ≥1 strain | ≥2 strains | ≥3 strains |
| Fluzone | 90.2 | 49.6 | 7.0 |
| Placebo | 16.4 | 0.9 | 0 |

*All comparisons to placebo are significant at the 0.05 level.

Figure 2:
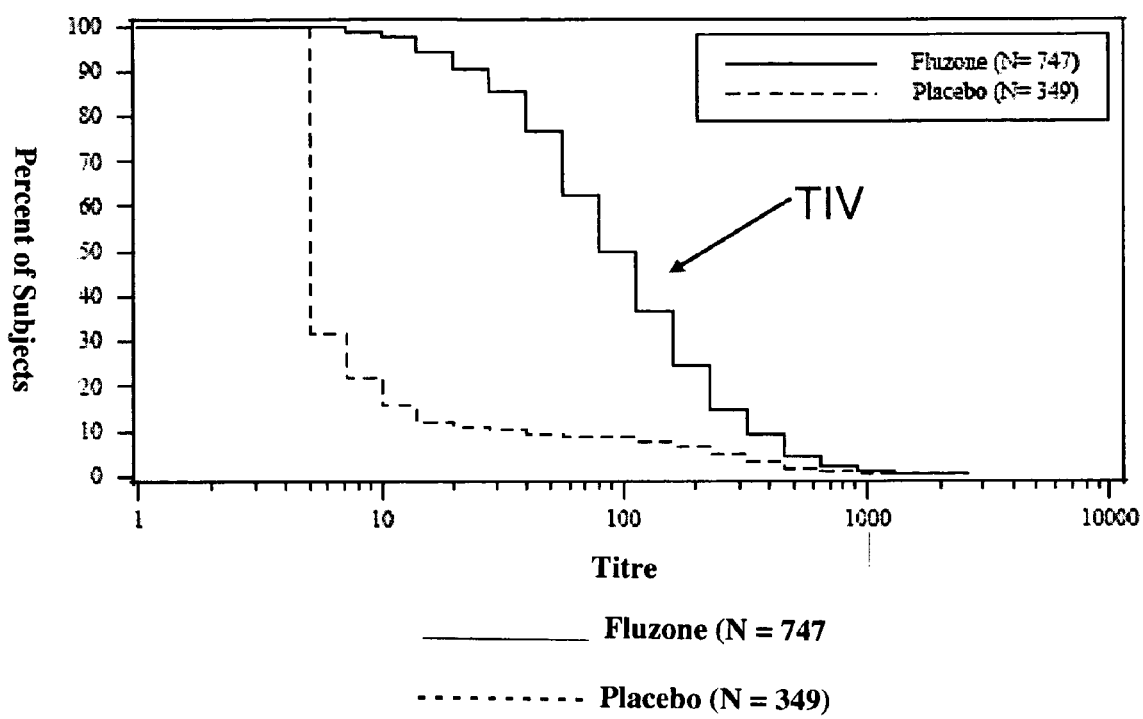
FIG. 2. Reverse cumulative distribution curve showing the immune response against Influenza A/H3N2.
Figure 3:
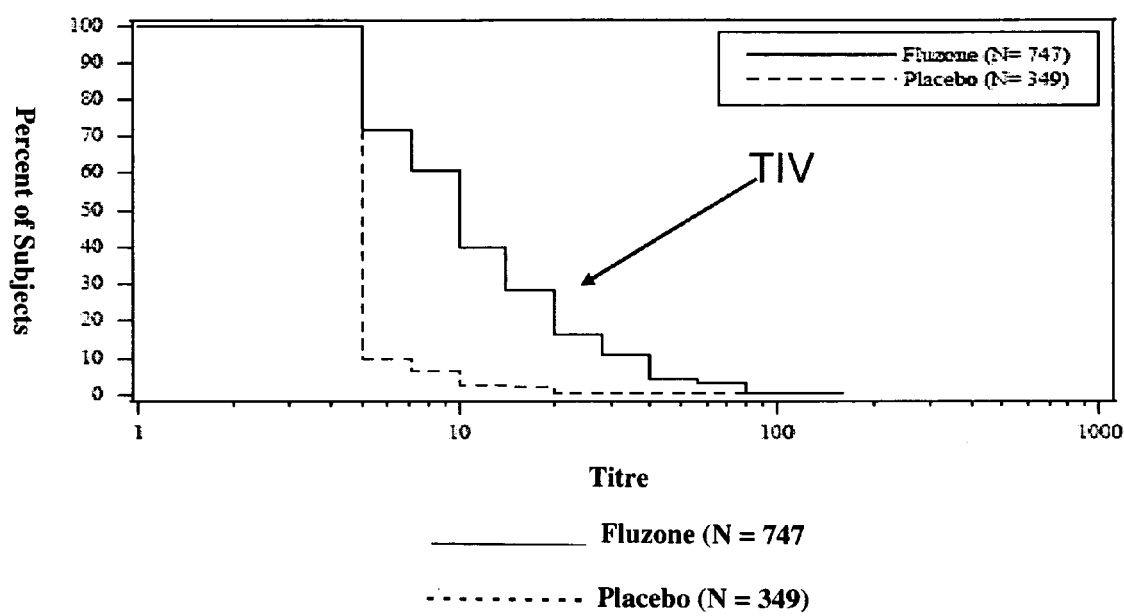
FIG. 3. Reverse cumulative distribution curve showing the immune response against Influenza B.

Immunogenicity to Fluzone in young children is also demonstrated by reverse cumulative distribution curve in FIGS. 1, 2 and 3.

The immunogenicity data generated in GRC28 was compared to that observed in older children, as shown in Tables VI and VII. Since 2003, a small (30 subjects) annual safety and immunogenicity study has been conducted in infants 6-35 months of age who received 2 doses Fluzone in order to generate serum banks for CDC, WHO, and sanofi pasteur. Those data were pooled and stratified by age to provide a context for the trials in younger children described herein. The number of seroconverters for each of H1N1, H3N2 and B in the 6-12 week old group was comparable (and higher in certain cases such as H3N2) than that observed in any of the other groups.

TABLE VI

| 2003-5 Annual Fluzone Pediatric Studies Pooled Immunogenicity Results vs GRC28 | | | | |
|---|---|---|---|---|
|  |  | Seroprotection Rates (Percent ≥1:40) | | |
| Age group | N | H1N1 | H3N2 | B |
| 6-12 Wks, GRC28 | ~746 | 50% | 86% | 11% |
| 6.0-9.1 Mo | 16 | 25% | 31% | 19% |
| 9.1-18.7 Mo | 36 | 47% | 61% | 36% |
| 18.7-36.0 Mo | 36 | 42% | 58% | 28% |
| Total | 88 | 41% | 55% | 30% |

TABLE VII

| 2003-5 Annual Fluzone Pediatric Studies Pooled Immunogenicity Results vs GRC28 | | | | |
|---|---|---|---|---|
|  |  | GMT (95% CI) | | |
| Age Group | N | H1N1 | H3N2 | B |
| 6-12 Wks, GRC28 | ~746 | 33 (30, 36) | 95 (88, 102) | 11 (10.8, 12.0) |
| 6.0-9.1 Mo | 16 | 23 (14, 37) | 20 (9, 43) | 13 (8, 22) |
| 9.1-18.7 Mo | 36 | 48 (32, 73) | 76 (42, 139) | 24 (16, 37) |
| 18.7-36.0 Mo | 36 | 41 (25, 68) | 81 (40, 162) | 24 (15, 39) |
| Total | 88 | 40 (30, 52) | 61 (41, 91) | 22 (17, 28) |

It was also very important to understand whether the children involved in this trial exhibited any significant side effects. This was not the case, as shown in Tables VIII and IX.

TABLE VIII

| Fever Rates within 3 Days of First or Second Dose | | | |
|---|---|---|---|
|  | Fluzone | Placebo | Difference in proportion, Fluzone vs. Placebo (95% CI) |
| First Dose | 11.2% | 11.7% | −0.5% (−4.2%, 3.2%) |
| Second Dose | 2.3% | 3.8% | −1.6% (−3.7%, 0.5%) |

All standard childhood vaccines given concomitantly at Dose 1. Non-inferiority was established in this population.

TABLE VII

| Solicited Reaction Rates Within 3 Days after Dose 1* | | |
|---|---|---|
| Reaction | Fluzone | Placebo |
| Irritability | 80% | 78% |
| Appetite Lost | 39% | 42% |
| Vomiting | 15% | 12% |
| Crying Abnormal | 62% | 62% |
| Drowsiness | 67% | 65% |
| Injection Site Tenderness | 64% | 69% |
| Inj Site Erythema | 14% | 12% |
| Inj Site Swelling | 12% | 11% |

This data revealed no significant differences between those children receiving Fluzone and those receiving placebo.

TABLE VIII

Solicited Reaction Rates Within 3 Days after Dose 2*

| Reaction | Fluzone | Placebo |
|---|---|---|
| Irritability | 55% | 57% |
| Appetite Lost | 22% | 23% |
| Vomiting | 11% | 9.4% |
| Crying Abnormal | 41% | 39% |
| Drowsiness | 41% | 40% |
| Injection Site Tenderness | 41% | 41% |
| Inj Site Erythema | 6% | 5% |
| Inj Site Swelling | 5% | 3% |

This data revealed no significant differences between those children receiving Fluzone and those receiving placebo. The number of serious adverse events (SAE) was also similar between the Fluzone and placebo groups (2.1% and 1.7%, respectively).

A second clinical trial (GRC27) was also conducted and revealed similar results. The immunogenicity data from that trial is summarized in Tables IX through XII below.

TABLE IX

Geometric Mean Titers at Post-Dose 2 (GRC27)

| | Flu A/NC/20/99 | Flu A/W/03/2003 | Flu B/J/10/2003 |
|---|---|---|---|
| 6-12 Weeks | 27.6 | 46.3 | 8.4 |
| 24-36 Weeks | 47.0 | 90.9 | 15.3 |

TABLE X

Seroprotection Rates (≥40) at Post-Dose 2 (GRC27)

| | Flu A/NC/20/99 | Flu A/W/03/2003 | Flu B/J/10/2003 |
|---|---|---|---|
| 6-12 Weeks | 45.6 | 59.1 | 4.8 |
| 24-36 Weeks | 69.4 | 77.8 | 21.5 |

TABLE XI

Seroprotection Rates (>40) at Post-Dose 2 in 2-month olds, All Subjects vs. Influenza Antibody-Naive Subjects (GRC27)

| | Flu A/NC/20/99 | Flu A/W/03/2003 | Flu B/J/10/2003 |
|---|---|---|---|
| 6-12 Weeks (all) | 45.6 | 59.1 | 4.8 |
| 6-12 Weeks (naïve) | 70.4 | 67.6 | 3.2 |

TABLE XII

Proportion of Subjects Achieving ≥40 in at Least One Influenza Strain (GRC27)

| | At least 1 of 3 |
|---|---|
| 6-12 Weeks (all) | 75.5 |
| 6-12 Weeks (naïve) | 87.5 |

It can be concluded from the data generated in these trials that Fluzone TIV is immunogenic in children less than 6 months old. It can also be concluded that Fluzone TIV has an acceptable safety profile in children less than 6 months old. Thus, it was shown herein that delivering influenza vaccine to two month old infants was well accepted, was safe, and immunogenic. Adding influenza vaccine to the routine infant vaccine schedule would enhance immunization of a vulnerable population without requiring extra medical visits and would increase flexibility in providing influenza vaccine to the young children at highest risk for hospitalization due to influenza.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method of immunizing a child under six months of age against H1N1 influenza, H3N2 influenza, influenza B and inducing immune responses against DTaP, Hib conjugate and inactivated polio, comprising:
    administering to the child an effective amount of a pharmaceutical composition comprising a trivalent influenza vaccine comprising hemagglutinin (HA) of an influenza H1N1 virus, an influenza H3N2 virus and an influenza B virus; and
    concomitantly administering an effective amount of vaccines that include DTaP, Hib conjugate, and inactivated polio.

2. The method of claim 1, wherein the trivalent influenza vaccine comprises at least one split virus.

3. The method of claim 1, wherein the pharmaceutical composition is administered intramuscularly.

4. The method of claim 1, wherein the trivalent influenza vaccine comprises at least one whole inactivated virus.

5. The method of claim 1, wherein the trivalent influenza vaccine comprises at least one live attenuated virus.

6. The method of claim 1, wherein the trivalent influenza vaccine comprises an adjuvant.

7. The method of claim 1, wherein the child is 6 to 12 weeks of age.

8. The method of claim 1, wherein the method further requires inducing immune responses against hepatitis B by also concomitantly administering an effective amount of a hepatitis B vaccine.

* * * * *